(12) United States Patent
Ribnicky et al.

(10) Patent No.: US 7,033,618 B2
(45) Date of Patent: Apr. 25, 2006

(54) METHODS OF ADMINISTERING GAULTHERIN-CONTAINING COMPOSITIONS

(75) Inventors: David M. Ribnicky, Plainsboro, NJ (US); Alexander A. Poulev, Highland Park, NJ (US); Ilya Raskin, Manalapan, NJ (US)

(73) Assignee: Rutgers University, The State University of New Jersey, New Brunswick, NJ (US)

( * ) Notice: Subject to any disclaimer, the term of this patent is extended or adjusted under 35 U.S.C. 154(b) by 418 days.

(21) Appl. No.: 10/338,312

(22) Filed: Jan. 8, 2003

(65) Prior Publication Data

US 2003/0161898 A1 Aug. 28, 2003

Related U.S. Application Data

(63) Continuation-in-part of application No. 09/887,766, filed on Jun. 21, 2001, now abandoned, which is a continuation-in-part of application No. 09/258,597, filed on Feb. 26, 1999, now abandoned.

(51) Int. Cl.
*A61K 35/78* (2006.01)
(52) U.S. Cl. .................................................. 424/725
(58) Field of Classification Search ................. 424/725
See application file for complete search history.

(56) References Cited

U.S. PATENT DOCUMENTS

| | | | | |
|---|---|---|---|---|
| 3,615,702 | A * | 10/1971 | Swisher | 426/98 |
| 3,954,978 | A * | 5/1976 | Magolan | 424/773 |
| 4,021,439 | A | 5/1977 | Krenzer | |
| 5,176,913 | A | 1/1993 | Honerlagen et al. | 424/195.1 |
| 5,294,434 | A | 3/1994 | King et al. | 424/58 |
| 5,592,956 | A * | 1/1997 | Ju et al. | 131/270 |
| 5,633,027 | A * | 5/1997 | Cherukuri et al. | 426/96 |
| 5,698,181 | A * | 12/1997 | Luo | 424/49 |
| 2002/0031562 | A1 | 3/2002 | Ribnicky et al. | |

OTHER PUBLICATIONS

Balick et al., "Plants, People, and Culture," *Scientific American Library*, New York, p. 32 (1997).
Barnaulov et al.,. "Chemical Composition and Initial Assessment of Pharmacologic Properties of Preparations Made of *Filipendula Ulmaria* (L) Maxim Flowers" (Translated), *Rastit. Resur.*, 13(4): 661-669 (1977).
Barnett et al., eds. "Acetylsalicylic Acid, New Uses for an Old Drug," Raven Press, New York (1982) (Table of Contents only).
Bishop, "Botanicals in Bath Care, Herbal extracts and Aromatic Essential Oils Have Been Used for Centuries to Yield Benefits Now Sought by Society," *Cosmetics & Toiletries*, 104:65-69 (1989).
Bridel et al., "Etude biochimique sur la composition du Monotropa Hypopitys L. Obtention d'un nouveau glucoside à salicylate de méthyle, la monotropitine," *Comptes Rendus*, pp. 642-644 (1923).
Bridel et al., "Sur l'hydrolyse fermentaire de la monotropitine. Obtention du primevérose," *Comptes Rendus*, pp. 991-993 (1924).
Bridel et al., "Sur un complexe glucosidique instable de l'écorce de tige de Nerprun purgative (Rhamnus cathartica L.)," *Comptes Rendus*, pp. 857-860 (1925).
Bridel et al., "Le primevérose, les primevérosides et la primevérosidase," *Comptes* Rendus, 1421-1423 (1925).
Bridel et al., "Sur la préparation et les propriétés du monotropitoside," *Comptes Rendus*, pp. 1864-1866 (1925).
Bridel et al., "Le glucoside á salicylate de méthyle du Gaultheria procumbens L. ést le monotropitoside," *Comptes Rendus*, pp. 609-611 (1928).
Butler et al., "Prolongation of Rat Tail Bleeding Time Cause by Oral Doses of a Thromboxane Synthetase Inhibitor Which Have Little Effect on Platelet Aggregation," *Thrombosis Hemostasis*, 47:46-49 (1982).
Cohen et al., "$^{13}C_6$-[Benzene Ring]-Indole-3-Acetic Acid, A New Internal Standard for Quantitative Mass Spectral Analysis of Indole-3-Acetic Acid in Plants," *Plant Physiol.*, 80:14-19 (1986).
Dejana et al., "Bleeding Time in Laboratory Animals II—A Comparison of Different Assay Conditions in Rats," *Thrombosis Research*, 15:191-197 (1979).

(Continued)

*Primary Examiner*—Michael Meller
(74) *Attorney, Agent, or Firm*—Marshall, Gerstein & Borun LLP (57) ABSTRACT

The present disclosure provides methods for obtaining gaultherin, a natural salicylate derivative, from plant tissue. The methods involve preventing the hydrolysis of the gaultherin in the plant tissue by disrupting the plant tissue under solvent conditions lacking a drying agent. The disclosure further provides various forms of plant-derived gaultherin, including alcoholic extracts, aqueous solutions and dried preparations, all suitable for use as a natural aspirin substitute. Moreover, the disclosure provides methods of using gaultherin-containing compositions to increase serum salicylic acid, to treat cancer cells, to treat cardiovascular (e.g., cardiopulmonary) conditions, to treat anti-inflammatory responses, and to inhibit cyclooxygenase.

8 Claims, 3 Drawing Sheets

OTHER PUBLICATIONS

Enyedi et al., "Localization, conjugation, and function of salicylic acid in tobacco during the hypersensitive reaction to tobacco mosaic virus," *Proc. Nat'l. Acad. Sci. (USA)*, 89:2480-2484 (1992).

Goris et al., "Caractères et composition du Primevérose," *Comptes Rendus*, 871-873 (1919).

Guth et al., "Topical Aspirin Plus HCl Gastric Lesions in the Rat," *Gasrtoenterology*, 76:88-93 (1979).

Kayser et al., "Local and remote modifications of nociceptive sensitivity during carrageenin-induced inflammation in the rat," *Pain*, 28:99-107 (1987).

Miller et al., "Reporting Results of Cancer Treatment," *Cancer*, 47(1):207-214 (1981).

Nunez et al., "Specific Inhibition of PAF-Acether-Induced Platelet Activation By BN 52021 And Comparison With The PAF-Acether Inhibitors Kadsurenone And CV 3988," *European Journal of Pharmacology*, 123:197-205 (1986).

Onions, "Botanicals—Back to Basics Part 2," *Soap Perfumery & Cosmetics*, 64(11):57-59 (1991).

Perry et al., "Health Effects of Salicylates in Foods and Drugs," *Nutrition Reviews*, 54(8):225-240 (1996).

Pierpoint, "Salicylic Acid and its Derivatives in Plants: Medicines, Metabolites and Messenger Molecules, " *Advances in Botanical Research*, 20:164-235 (1994).

Procter, Jr., "Observations on the Volatile Oil of Betula Lenta, and on Gaultherin, a Substance Which, by Its Decomposition, Yields that Oil," *The American Journal of Pharmacy*, IX(IV), pp. 22, 242-250 (1844).

Raskin et al., "Salicylic Acid Levels in Thermogenic and Non-Thermogenic Plants," *Annals of Botany*, 66:369-373 (1990).

Ren et al., "Inflammatory Models of Pain and Hyperalgesia," *ILAR Journal*, 40(3):111-118 (1999).

Ribnicky et al., "Intermediates of Salicylic Acid Biosynthesis in Tobacco," *Plant Physiol.*, 118:565-572 (1998).

Ribnicky et al., "Determination of salicylates in *Gaultheria procumbens* by LC-MS and GC-MS," (Abstract) (Aug., 1999).

Ribnicky et al., Development of PMI-5001, a Natural Salicylate from *Gaultheria procumbens* for Cardiovascular Health, (Abstract) (Jan., 2002).

Robertson et al., "Syntheses of Glucosides, Part VIII, The Synthesis of Monotropitoside (*Gaultherin*),"*J. Amer. Chem. Soc.*, 1881-1888 (1931).

Scott et al., "Mass Spectrometic Quantification of Salicylic Acid in Plant Tissues," *Phytochemistry*, 37(2):335-336 (1994).

Shimura et al., "Docosahexanoic Acid (DHA) Improved Glucose and Lipid Metabolism in KK-$A^y$ Mice with Genetic Non-Insulin-Dependent Diabetes Mellitus (NIDDM)," *Biol. Pharm. Bull.*, 20(5):507-510 (1997).

Towers et al., "Phenolic Acids and Phenolic Glycosides of *Gaultheria* Species," *Phytochemistry*, 5:677-681 (1966).

Tyler et al., eds. "Gaultheria Oil," *Pharmacognosy, $8^{th}$ Edition*, Lea & Febiger, Philadelphia, pp. 142-143 (1981), Yeo et al., "Phytochemical Studies on the Constituents of *Filipendula glaberrima,*" *Korean Journal of Pharmacognosy*, 23(3):121-125 (1992).

Zhang et al., "Gaultherins A and B, two lignans from *Gaultheria yunnanensis,*" *Phytochemistry*, 51:469-472 (1999).

International Search Report for PCT/US01/20008 dated Sep. 26, 2001.

Written Opinion for PCT/US01/20008 dated May 7, 2003.

International Search Report for PCT/US03/02502 dated May 5, 2003.

\* cited by examiner

METHODS OF ADMINISTERING GAULTHERIN-CONTAINING COMPOSITIONS

CROSS REFERENCE TO RELATED APPLICATIONS

This is a continuation-in-part of U.S. patent application Ser. No. 09/887,766, filed Jun. 21, 2001 now abandoned, which is a continuation-in-part of U.S. patent application Ser. No. 09/258,597, filed Feb. 26, 1999 now abandoned, the respective disclosures of which are incorporated herein by reference in their entireties, and the 35 U.S.C. § 120 benefit of which are claimed.

FIELD OF THE DISCLOSURE

This disclosure relates to pharmaceutically active compounds obtained from natural sources. More specifically, the disclosure relates to methods of treating and preventing cancer, cardiovascular conditions, including cardiopulmonary conditions, and inflammatory responses by administering compositions containing a salicylate derivative, gaultherin, isolated from plant sources, particularly *Gaultheria procumbens*.

BACKGROUND OF THE DISCLOSURE

The medical benefits of plant salicylates have been enjoyed by people for centuries. Salicylic acid was first isolated in 1839 from the flower buds of an herb, *Filipendula ulmaria*, which is also sometimes referred to as *Spiraea ulmaria*. The benefits of plant-derived salicylates prompted intensive research, which led to the commercial production of synthetic acetylsalicylic acid (aspirin) in 1899. Today, aspirin (acetylsalicylic acid) is probably the most widely used drug in the world because of its antipyretic, anti-inflammatory, and analgesic properties.

The development of the acetylated form of salicylate was prompted by the need for a form of the drug that would not cause the gastrointestinal distress associated with the use of salicylic acid. Indeed, acetylsalicylic acid has been shown to have fewer side effects than salicylic acid. Nonetheless, acetylsalicylic acid can promote similar problems.

Most of the pharmacological activity of acetylsalicylic acid is due to the production of salicylic acid. Some noteworthy activities of salicylic acid include general anti-inflammatory properties, increased fibrinolysis, inhibition of glycosaminoglycan synthesis, inhibition of the lipoxygenase pathway, reduction of T-cell adhesion, free radical scavenging, inhibition of prostaglandin biosynthesis, and some anti-carcinogenesis activities.

As mentioned, acetylsalicylic acid was synthesized as a derivative of salicylic acid that exhibited fewer side effects when administered as a therapeutic. Efforts have been made to derivatize salicylic acid and aspirin in various ways to further mitigate gastric irritation. The general strategy for reducing gastric upset has been to chemically derivatize the salicylate molecule to delay the release of free salicylic acid until after it has passed from the stomach.

Wintergreen, or *Gaultheria procumbens*, contains a very high concentration of salicylate derivatives, reaching concentrations exceeding 10 mg per gram fresh weight of tissue. This concentration is over 20-fold greater than the total salicylate concentration (salicylate and any derivates combined) found in *Filipendula*, the plant from which salicylic acid was first isolated. Reports disclosing the presence of gaultherin (a salicylate derivative described below) in *Filipendula* tissues, but not gaultherin recovery yields, are found, e.g., in the abstracts of Barnaulov et al., *Rastit. Resur.*, 13(4):661–669 (1977) and Yeo etal., *Saengyak Hakhoechi*, 23(3):121–125 (1992).

Methyl salicylate, also known as oil of wintergreen, is responsible for the smell and taste of wintergreen. Although methyl salicylate can be toxic when ingested at concentrations used for topical application, this ester has been shown to have decreased ulcerogenic activity when compared with an equal dose of salicylic acid, as measured by the respective salicylate contents.

Gaultherin consists of methyl salicylate conjugated to the disaccharide, primeverose. When plant tissues are disrupted, the endogenous gaultherin is rapidly lost, presumably by enzymatic hydrolysis with the release of methyl salicylate. This process presumably occurs as a protective mechanism for the plant.

In 1844, Proctor defined gaultherin as a conjugate of methyl salicylate with glucose but claimed that it did not exist within the plant for which it was named. Interest in such conjugates did not recur until nearly 60 years later, when a series of articles was published in France. The authors of these articles [Bridel and Gillon, *Comptes Rendus*, pp. 609–611 (1928); Bridel and Guignard, *Comptes Rendus,* pp. 857–860 (1925); Bridel and Guignard, *Comptes Rendus*, pp. 1421–1423 (1925); Bridel and Guignard, *Comptes Rendus*, pp. 642–644 (1923); Bridel and Guignard, *Comptes Rendus*, pp. 991–993 (1923); Goris et al., *Comptes Rendus*, pp. 871–873 (1919)] described the sugars of these conjugates and defined monotropidoside as a conjugate of methyl salicylate with primeverose, which is a disaccharide of xylose and glucose. These studies were performed with various species, and led to the occurrence of excessive terminology.

*Gaultheria procumbens* was not examined until 1928, when it was determined that monotropidoside was gaultherin and that gaultherin could only be extracted from *Gaultheria* with boiling water and calcium carbonate, followed by a series of solvent extractions, including 95% alcohol distillation, extraction with boiling hydrated acetic ether and addition of 95% alcohol [Bridel and Gillon, *Comptes Rendus*, pp 609–611 (1928)], which gave a final yield of 4 g/kg fresh weight plant material. These combined observations defined gaultherin as a conjugate of methyl salicylate with a disaccharide of xylose and glucose. These references also described an enzymatic activity leading to the hydrolysis of this conjugate; the activity has been attributed to gaultherase, an enzyme known only by its activity. Those terms have been perpetuated by the literature but no current investigations have been performed on either the conjugate or the enzyme. The previous work was summarized in 1931 [Robertson et al., *J Am. Chem. Soc.*, 1881–1888 (1931)], along with a description of the synthesis of gaultherin. Any current literature which includes the terms gaultherin or gaultherase appears to use these terms as defined in the original sources.

An effective method for obtaining useful quantities of gaultherin from natural plant sources is not currently available. The difficulty in obtaining gaultherin from plant tissue resides in the labile or unstable-nature of gaultherin extracts. Upon disruption of the plant tissue, the molecule is immediately hydrolyzed to its individual components, methyl salicylate and the disaccharide primeverose. As noted above, the hydrolysis is believed to be catalyzed by an enzyme referred to as gaultherase [see Robertson et al., *J. Am. Chem. Soc.*, pp. 1881–1889 (1931), and references cited therein].

Regardless of the means by which the hydrolysis occurs, it appears to be immediate and essentially complete, inasmuch as it has led some investigators to conclude that certain plants, most notably *Gaultheria procumbens*, do not contain gaultherin [see Proctor, *Am. J. Pharmacol.*, Vol IX, No. IV., pp. 22 and 242–250 (1844)].

Compounding the problem is the relatively hydrophilic nature of both gaultherin and the gaultherase activity. Attempts to maximize yield by using an aqueous solvent would lead to high losses due to gaultherase activity; using a non-aqueous or non-polar solvent would lead to lower than maximal yields because of the relatively lower solubility of gaultherin in such solvents, although the gaultherin might be expected to be relatively stable due to a correspondingly lower yield of the destructive gaultherase activity.

U.S. Pat. No. 5,176,913, issued Jan. 5, 1993, to Honerlagen et al. describes a method for preparing a partial extract containing the volatile-in-steam components and further lipophilic components of various plants. Among many plant species, *Gaultheria procumbens L.* is disclosed as a plant from which an extract can be obtained. Honerlagen teaches a method in which a drying agent is brought into contact with a crude extract to reduce or eliminate the water content of the extract. As disclosed by Honerlagen, the extraction invariably involves the removal of water, whether by use of chemical drying agents or by use of mechanical drying agents such as membrane technology.

Honerlagen isolates lipophilic plant compounds, including both volatile-in-steam and non-volatile-in-steam compounds. Lipophilic compounds are generally recognized in the art as being hydrophobic compounds which are generally not soluble in water. There is no recognition or appreciation in Honerlagen of a method that allows the separation and recovery of gaultherin from any accompanying gaultherase activity to protect gaultherin from hydrolysis. Further, Honerlagen fails to suggest any use for a gaultherin-containing extract.

Thus, a method for recovering gaultherin from plants by extraction under aqueous conditions suitable for extraction of the water-soluble gaultherin while reducing or eliminating gaultherin degradation or destruction, such as hydrolysis due to a gaultherase activity, would be a significant advance.

Additionally, the provision of a therapeutic agent which may be administered to treat inflammatory responses and cardiovascular conditions, including cardiopulmonary conditions, without causing substantial gastrointestinal discomfort would also represent a significant advance.

Furthermore, the provision of methods wherein serum salicylic acid concentrations are increased, without causing substantial gastrointestinal discomfort, would also be a significant contribution to the art, as would the provision of methods of inhibiting tumor cell growth and cyclooxygenase activity, without causing substantial gastrointestinal discomfort.

SUMMARY OF THE DISCLOSURE

The present disclosure provides a solution to the aforementioned problem by providing a convenient method of obtaining gaultherin, as opposed to its products of hydrolysis, from natural plant sources, particularly *Gaultheria procumbens*. Contrary to prior reports which suggest otherwise, the majority of salicylate present in *G. procumbens* is found in a form called gaultherin. The present disclosure also provides plant extracts containing gaultherin and purified gaultherin obtained from such plant sources, for use as a natural aspirin analog exhibiting minimal gastric side effects.

According to one aspect of the present disclosure, a plant extract containing gaultherin is provided. Preferably, the extract is obtained from *Gaultheria procumbens*, and preferably, a yield of at least 5 mg gaultherin per gram fresh weight plant material is obtained. The high yield of gaultherin is achieved by extracting fresh or frozen plants or plant parts, such as those obtained from *Gaultheria procumbens*, in a solvent lacking a compound or structure for removing water (i.e., a drying agent such as tragacanth, gelatin, a water-free sodium sulfate, a water-free magnesium sulfate, a water-free calcium chloride, a molecular sieve, membranes, or combinations thereof, as examples of compounds and structures that bind, absorb, adsorb, or capture water molecules) for purposes of removing or reducing the water content in a mixture or composition.

In particular, the gaultherin is recovered in a solvent that has sufficient polarity to retain gaultherin while reducing the level of a gaultherase activity. Preferably, no more than 20% of the gaultherase activity is recovered (relative to the activity recovered using a suitably buffered water solvent under otherwise comparable extraction conditions); more preferably, no more than 5% of the gaultherase activity is recovered, and most preferably, no more than 1% of the gaultherase activity is recovered.

The methods of the disclosure thus provide improved yields of gaultherin in plant extracts, which are useful as nutraceutical compositions and as therapeutics. Preferably, the extract comprises at least 10 mg gaultherin per gram fresh weight (gfw) plant material, more preferably at least 15 mg/gfw, even more preferably at least 20 mg/gfw, and most preferably it comprises at least 25 mg gaultherin per gram fresh weight plant material. In a preferred embodiment, the extract is an alcoholic extract wherein the alcohol is selected from the group consisting of methanol, ethanol, and isopropanol. In a more preferred embodiment, gaultherin is present in an ethanolic extract and can be ingested or applied, or incorporated into a nutraceutical or pharmaceutical composition for ingestion or application to a mammal such as a human. In another preferred embodiment, a dried or powdered preparation of gaultherin obtained from the alcoholic extract or an aqueous resuspension thereof is provided.

According to another aspect of the disclosure, a method is provided for obtaining gaultherin from plants. Preferably, the plant is *Gaultheria procumbens*, and, preferably, the method yields gaultherin in an amount of at least 5 mg, preferably at least 10 mg, more preferably at least 15 mg, even more preferably at least 20 mg, and most preferably at least 25 mg per gram fresh weight plant material. The method comprises: (a) providing fresh or fresh-frozen plant material; and (b) disrupting the tissue under solvent conditions lacking a drying agent that reduce the likelihood of hydrolysis of gaultherin, thereby producing an extract of the tissue. Suitable solvents will have sufficient polarity to retain gaultherin, while reducing the recovery yield of any gaultherase activity. Preferably, the tissue is disrupted in the presence of an alcohol solvent to produce an alcoholic extract. In a preferred embodiment, the alcohol is ethanol.

In related embodiments, the method may further comprise removing particulate plant material from the extract. In addition, the method may be extended to provide a powdered (i.e., solid) preparation of a gaultherin-containing composition prepared by drying the extract. Where the extract is dried, it is preferred that the extract is exposed to a compound that removes all solvent components, including, for example, aqueous, non-polar, and polar fluids.

In yet another embodiment, the method further comprises adding water to the dried extract, thereby producing an aqueous solution of gaultherin. The aqueous solutions, another aspect of the disclosure, also may be dried to produce a more purified solid form of gaultherin.

The extracts, aqueous solutions, and solid residue containing gaultherin (i.e., gaultherin-containing compositions) described herein can be used to advantage as a natural aspirin substitute which is less gastrically irritating than aspirin. For example, such gaultherin-containing compositions may be used to treat cardiovascular or cardiopulmonary conditions, inflammatory responses, and cancerous cells, and to inhibit cyclooxygenase activity.

From the foregoing, it can be seen that gaultherin possesses all the features of an ideal natural analog of aspirin. Gaultherin is found in plant tissues at high concentrations and is an extensively derivatized form of salicylate, which causes minimal gastric side effects. Accordingly, gaultherin should prove to be an effective natural substitute for synthetic aspirin, to be taken on a daily basis for general cardiovascular or cardiopulmonary benefit, or on an as-needed basis as a pain reliever and/or anti-inflammatory agent.

Other features and advantages of the present disclosure will be better understood by reference to the drawings, detailed description and examples that follow.

BRIEF DESCRIPTION OF THE DRAWINGS

FIGS. 3A and 3B. Liquid chromatography/mass spectrometry of bound forms of salicylate from wintergreen (*Gaultheria procumbens*).

DETAILED DESCRIPTION OF THE DISCLOSURE

Prior to the present disclosure, no method had been available for isolating significant amounts of gaultherin from plant tissue, due to the rapid degradation of the molecule into its components, methyl salicylate and primeverose, upon disruption of the plant tissue. As a result, this useful and advantageous form of salicylate has gone unexploited.

In accordance with the present disclosure, it has now been discovered that gaultherin can be isolated intact from plant tissue, using a simple process that inhibits the aforementioned hydrolytic breakdown of the molecule. This process is most advantageously applied to the wintergreen plant, which, surprisingly in view of reports to the contrary, has now been discovered to have a very high gaultherin content as compared to other selected plant species. The description below exemplifies wintergreen as the plant of choice for obtaining significant quantities of gaultherin. However, it will be appreciated by persons skilled in the art that the same methods could be applied to any plant species containing gaultherin or a similar salicylate derivative, with an expectation of obtaining intact gaultherin or similar derivative in high proportion to whatever amount is contained within that species.

The rapid hydrolysis of gaultherin to form methyl salicylate and the disaccharide, primeverose, has been attributed to an enzymatic activity referred to as "gaultherase." Gaultherase has never been isolated, so it is as yet unproven as to whether the hydrolysis of gaultherin is catalyzed by an enzyme. Regardless of the mechanism by which hydrolysis occurs, however, it is clear that disruption of the cells of gaultherin-containing plant tissue results in immediate hydrolysis of gaultherin. Disclosed herein is the discovery that this hydrolytic activity, whatever its cause, can be inhibited by disrupting the plant tissue in the presence of alcohol. It is believed that the alcohol inhibits the enzymatic activity of gaultherase, but other mechanisms may also play a role. It is also expected that other solvents, as listed below, or boiling water, will act in a manner similar to alcohol, to inhibit hydrolysis of gaultherin upon disruption of the plant cells.

Thus, disclosed herein is an extraction method for obtaining high yields of gaultherin or similar salicylate conjugates (e.g., other forms of sugar-conjugated methyl salicylate) from plant sources, particularly *Gaultheria procumbens*. In its most basic form, the method comprises the following steps: (1) provide fresh or fresh-frozen plant material; (2) optionally, freeze the tissue in liquid nitrogen; and (3) grind or otherwise disrupt the tissue in a solution containing a sufficient amount of alcohol (e.g., ethanol) or other solvent lacking a drying agent. The frozen, macerated tissue can be stored frozen for further processing. The extract may be further processed in the following steps: (4) remove solid matter from the alcoholic extract; (5) subjecting the alcoholic extract to an agent that removes solvent components to produce a solid (powdered) gaultherin-containing residue; (6) re-suspend the resulting alcoholic extract in an aqueous solution; and (7) after removing any water insoluble material, repeating step (5) to form a more purified form of gaultherin.

Using the aforementioned extraction procedure on *Gaultheria procumbens*, gaultherin has been obtained from above-ground plant parts in the amount of about 1 to about 26 mg per gram fresh weight tissue. The sections below describe each step of the extraction process in greater detail.

As mentioned above, the plant species chosen for obtaining gaultherin plays a very important role in how much gaultherin can be obtained from the plant source. *Gaultheria procumbens* contains a very high concentration of salicylate, mainly in the form of gaultherin (see Example 1). However, other plant species also contain significant amounts of bound salicylate, and could be used instead of *Gaultheria procumbens* as a plant source of derivatized salicylate such as gaultherin. These include, but are not limited to, various members of the thyme family, such as English thyme, French thyme and lemon thyme. However, wintergreen far exceeds any of these plant species in bound salicylate content.

The cultivar of wintergreen plant, as well as growth conditions of the plants, also affect the gaultherin content of the plant. For instance, though cultivated wintergreen is not categorized into varieties, the type of plant cultivated on the west coast of the United States has been found to have a higher salicylate content than does the wintergreen cultivated on the east coast (see Table II of Example 1). Additionally, the conditions under which the plants are grown also affect their gaultherin content. In particular, the inventors have noted that plants subjected to stress conditions, such as heat stress, dehydration, and exposure to chemical elicitors, have a higher bound salicylate content than do plants not subjected to such conditions. Accordingly, one modification of the extraction method of the disclosure to maximize gaultherin yield is to stress the plants prior to harvesting them for the extraction.

The salicylate content in wintergreen plants also varies somewhat with the tissue type. As shown in Table IV of Example 1, flowers tend to have a higher salicylate content than do leaves, stems, and berries. Thus, another modification of the extraction method of the disclosure is to use only wintergreen flowers as the starting plant material. However, a more feasible alternative is to use all above-ground plant parts, inasmuch as the leaves, stems, and berries of wintergreen do contain significant concentrations of salicylate, and it is much less labor intensive to simply harvest the entire plant.

In a preferred embodiment, fresh plant tissue is quick-frozen in liquid nitrogen, then ground or otherwise macerated (e.g., using a Polytron or a Waring blender) in alcohol. For this purpose, it is preferable to use an alcohol preparation containing 70–95% alcohol. However, preparations containing as little as 30% alcohol have been found reasonably effective for extracting gaultherin. Alcohols preferred for practice of the disclosure include lower alkyl alcohols, such as methanol, ethanol, and isopropanol. A particularly preferred alcohol for the extraction step of the disclosure is ethanol. A benefit of incorporating an ethanolic solvent in the extraction step of the disclosure is that gaultherin is surprisingly stable in an ethanolic solvent, which provides the advantage of an increased gaultherin yield or recovery. In addition, an ethanolic solvent is compatible with an ingestible nutraceutical product and, therefore, is suitable for incorporation into a pill, capsule, tablet, and other ingestible forms known in the art. It will be appreciated that any alcohol which inhibits the hydrolysis of gaultherin in the extraction process is contemplated for use in the present disclosure. Other alcohols suitable for use in the disclosure include, but are not limited to, n-propyl alcohol and any form of butanol, pentanol, or hexanol, among others. In addition, the initial extraction may be performed with other solvents, including, but not limited to, methylene chloride, acetonitrile, acetone, and chloroform. The initial extraction also may be performed with very hot water, preferably at the boiling point, which may, but need not, act by providing a suitably polar solvent for recovery of gaultherin while providing unsuitable conditions for recovery of an active form of a gaultherase activity.

The extract of plant material preferably is separated from the solids in the extract, e.g., by filtration, centrifugation, or any commonly known method. The gaultherin content of the extract may then be tested by known methods, or preferably, using any of the methods developed in accordance with the present disclosure, which are set forth in Example I. These include, but are not limited to, high performance liquid chromatography, liquid chromatography/mass spectrometry, and hydrolysis in acid followed by analysis by gas chromatography/mass spectrometry, as combined with stable isotope dilution analysis.

A solid residue containing gaultherin may be prepared by removing the solvent from the alcoholic extract. Preferably, the residue contains about 12% to about 18% (by weight) gaultherin. In a preferred embodiment of the disclosure, the alcohol extract is dried by removing the solvent therefrom, then the extract is re-dissolved in water or buffer. Water-insoluble materials are removed, e.g., by centrifugation, to prepare an aqueous solution containing gaultherin. In a further preferred embodiment, the aqueous solution is again reduced to dryness to produce a residue highly enriched in gaultherin.

Any of the preparations described above, i.e., the alcoholic or other solvent extract, aqueous solution or dried preparations, may be used as a natural alternative to acetylsalicylic acid, or "aspirin." The advantages of using gaultherin as an aspirin substitute include the fact that the compound is a "natural" compound, isolated from a plant source using a simple extraction process, as well as the fact that gaultherin is a highly derivatized salicylate that causes less gastric irritation than aspirin.

As previously set forth, the gaultherin-containing compositions may be used to treat cardiovascular conditions, including cardiopulmonary conditions. As used herein, cardiovascular and/or cardiopulmonary conditions refer to an abnormal, typically health threatening state of the cardiovasculature that may benefit from the treatment protocols disclosed herein.

The gaultherin-containing compositions may also be used to treat inflammatory responses (e.g., localized inflammation), including all conditions or disorders for which aspirin or its recognized therapeutic substitutes (e.g., ibuprofen, acetaminophen, naproxen, etc.) are indicated, including without limitation, headache (e.g., migraine), arthritis (e.g., rheumatoid) and other forms of joint pain or stiffness, general body aches, and other conditions for which an analgesic is indicated.

The alcoholic extract of gaultherin may be applied topically, or if prepared with an ingestible alcohol, may be administered orally or intranasally. Similarly, the aqueous solution of gaultherin may be administered orally or intranasally, or by any other means known for administration of aqueous solutions of acetylsalicylic acid. The dried gaultherin preparations can be tabletted or encapsulated or otherwise formulated for oral administration (e.g., in a gum or candy). For any of the liquid or solid formulations, the gaulthefin preferably is administered as a dosage unit. The term "dosage unit" refers to a physically discrete unit of the preparation appropriate for a patient undergoing treatment or using the compound for prophylactic purposes. Each dosage unit contains a quantity of active ingredient, in this case, total salicylates (corresponding to the moles of salicylic acid and derivatives thereof), calculated to produce the desired effect in association with the selected formulation.

As used herein, the term "therapeutically effective amount" refers to an amount of a gaultherin-containing composition which is sufficient to alleviate, ameliorate, prevent, and/or clear the symptoms and/or the pathology of a condition or disease contemplated to be treatable by salicylates. The methods in accordance with the disclosure contemplate administration of a gaultherin-containing composition whether or not symptoms are manifest, i.e., prophylactic administration is contemplated. Because preferred dosages of aspirin for a variety of therapeutic and prophylactic purposes are well known in the art, appropriate dosages of purified gaultherin and gaultherin-containing compositions may be easily determined by standard methods.

The following examples are provided to describe the disclosure in greater detail, and are intended to illustrate, not to limit, the appended claims.

EXAMPLE 1

Preparation of Gaultherin From *Gaultheria procumbens*

Wintergreen (*Gaultheria procumnbens*) is a small ericaceous plant found growing in the understory of dense forests and is also widely used in the landscape industry. Wintergreen is known for its constituent essential oil of wintergreen, which is comprised predominantly of methyl salicylate [Tyler et al., eds., *Pharmacognasy*, Lea & Febiger, Philadelphia, pp 103–143 (1981)]. In this example, the salicylate concentrations of several plant species are compared, and it is shown that wintergreen contains extraordinarily high concentrations of salicylates, which can reach concentrations of over 1% of the fresh weight of the tissue. The predominant form of this salicylate is gaultherin. Methods for obtaining gaultherin from plants, including *Gaultheria procumbens* are described.

Methods:

Measurement of SA using stable isotope dilution analysis. Plant tissue or extract samples (100–1000 mg) were ground in liquid nitrogen and extracted in 5 mL of 90% methanol as previously described [Ribnicky et al., *Plant Physiology*, 118:565–572 (1998)]. Samples which were not subjected to immediate analysis were stored at −80° C. $^2H_6$-SA (98% atom $^2H_6$ enriched, Isotec Inc., Miamisburg, Ohio.) dissolved in isopropanol was added to each sample as an internal standard in the amount of 0.5–1 µg, depending on the size of the sample and expected concentration of salicylate. The sample was extracted at 4° C. for 1 hour in a 13×100 mm test tube and centrifuged at 10,000 g for 10 min. The pellet was then rinsed with 1 mL 100% methanol followed by an additional centrifugation.

Free SA determination: The samples to be analyzed for free SA were processed in the same manner as for the free acids previously described [Ribnicky et al., *Plant Physiology*, 118:565–572 (1998)]. The free SA samples of wintergreen were processed using an alternative method as well to prevent any possible liberation of free SA from methyl salicylate. These samples were extracted in 50% isopropanol/100 mM phosphate buffer, pH 7 at 4° C. for 1 hour and diluted 10 fold with water. The sample extract was then partially purified on a 3 mL conditioned (rinsed with 2 mL of each methanol, water and 100 mM phosphate buffer, pH 7, followed by a rinse with 8 mL water) amino solid phase extraction column (J. T. Baker, Phillipsburg, N.J.). The sample was then eluted with 4% acetic acid/methanol, dried in vacuo, and methylated with ethereal diazomethane. The methylated sample was reduced to near dryness and resuspended in 25 µL of ethyl acetate for analysis by GC-MS-selected ion monitoring. The samples were manually injected in the splitless mode into a gas chromatograph (model 5890, Hewlett-Packard)/mass spectrometer (model 5971, Hewlett-Packard) equipped with a 30-m×0.25 mm DB-5MS fused silica capillary column (J&W Scientific, Folsom Calif.). Chromatographic parameters were as follows: injection temperature at 280° C., initial oven temperature at 500° C. for 3 min followed by a ramp at 30° C./min to 280° C. The monitored ions for native methyl salicylate were (m/z): 92, 120, and 152 and for the $^2H_6$-methyl salicylate were 96, 124, and 156. The concentration of the endogenous SA was then calculated based on the ratio of the major ion (120) of the native SA and the comparable ion (124) of the $^2H_6$-labeled internal standard using the equation of isotope dilution analysis described by Cohen et al., *Plant Physiology*, 80:14–19 (1986). These ratios were also confirmed using the abundance of the molecular ions of both forms (152 and 156). The decrease in mass from +6 to +4 for the deuterium-labeled internal standard is due to the exchange of the carboxyl and hydroxyl hydrogens of the molecule. The other 4 positions are non-exchangeable.

Total SA determination: The samples to be analyzed for total acids were also processed as previously described [Ribnicky et al., *Plant Physiology*, 118:565–572 (1998), Enyedi et al., *Proc. Natl. Acad. Sci.*, 89:2480–2484, (1992)], with modifications. The methanolic extract was resuspended in 2 mL of 2N NaOH and sealed in a 12×35 mm screw cap vial with a TFE lined cap prior to heating at 70° C. After 2 h, the sample was cooled on ice to 4° C. and then it was acidified with 250 µL of 36.9% HCl. The sample was then resealed and heated for an additional 1 hour at 70° C., cooled to 4° C. and partitioned twice with ethyl acetate:cyclopentane:2-propanol (100:99:1) and reduced in vacuo to dryness. After resuspending in 2 mL of 1% acetic acid, the sample was applied to a conditioned (rinsed with 2 mL each water, methanol and 0.5% acetic acid) $C_{18}$ SPE column (J. T. Baker), rinsed with 5 mL of water and eluted with 2 mL of acetonitrile, reduced to dryness, followed by derivatization and analysis as described above.

Measurement of methyl salicylate using stable isotope dilution analysis. Measurement of endogenous methyl salicylate was performed as previously described for benzaldehyde [Ribnicky et al., *Plant Physiology*, 118:565–572 (1998)]. $^2H_4$-methyl salicylate was added during the extraction for use as an internal standard. The $^2H_4$-methyl salicylate was custom synthesized for this purpose. Five hundred µg of $^2H_6$-SA dissolved in isopropanol was dried under a stream of nitrogen gas in a 12×35 mm screw cap vial and resuspended in 100 µL of methanol. One mL of ethereal diazomethane was then added to the labeled SA solution and the vial was sealed with a TFE lined cap. After 10 min, this mixture was reduced to near dryness with a stream of nitrogen gas and resuspended in 10 mL of isopropanol. The precise concentration of the $^2H_4$-methyl salicylate solution was adjusted to account for losses during chemical synthesis, thereby ensuring an accurate concentration for the labeled methyl salicylate standard. The degree of adjustment was small and was determined by mixing the $^2H_4$-labeled internal standard with known amounts of unlabeled methyl salicylate and comparing the abundance of the major ions of both molecular forms by GC-MS as described above for SA.

Similarly, endogenous methyl salicylate levels were calculated based on the ratio of the major ion (120) for native methyl salicylate and the comparable ion (124) of the $^2H_4$-labeled internal standard as described above.

HPLC and LC-MS analysis of gaultherin. In order to extract the conjugates of salicylate, fresh plant tissues or tissues which were stored frozen at −20° C. or lower, were frozen in liquid nitrogen and ground with a mortar and pestle. Tissues which were dried at 20° C. or 70° C. or freeze dried did not contain measurable concentrations of conjugate or methyl salicylate. Alcohol was then added to the tissue while it remained frozen in a volume at least 5-fold greater than the corresponding weight of the tissue. Alternatively, for larger extractions, fresh tissue was ground in a Waring blender at high speed in the presence of alcohol until the tissue became a suspension of fine particulates. Solid plant materials were then removed by centrifugation after a minimum incubation of 1 hour at 4° C. as described for the measurements of salicylates.

Extraction of wintergreen in alcohols, including methanol, ethanol and isopropanol, yields one predominant component as determined by HPLC (Waters) equipped with a Waters 996 photodiode array detector (PDA)(scan from 190–450 nm) and a Waters 474 scanning fluorescence detector (set at an excitation wavelength of 301 nm and an emission wavelength of 412 nm) using a $C_{18}$ column (Waters)(4.6 mm×150 mm). The column was equilibrated at a flow of 1.5 mL/min with 0.5% acetic acid:methanol (75:25 v/v) followed by a gradient to 25:75 starting at 3 min and ending at 10 min. The primary metabolite eluted at 5 min using these conditions. This metabolite was absent from water extracted tissues, which instead contained peaks with retention times and PDA spectra corresponding to salicylic acid and methyl salicylate. This conjugated form of methyl salicylate was relatively polar, but was better resolved with reverse phase HPLC using a shallow gradient from 5:95 to 25:75 (acetonitrile: 0.5% acetic acid in water) over 30 min with a $C_8$ column (4.6 mm×150 mm) and a flow rate of 1 mL/min. These conditions were used for the purification of the salicylate conjugate (by collecting the fraction at 17 min) and revealed the presence of a second form of bound salicylate (which eluted at 10 min). The minor form of bound salicylate which eluted early was not always detectable.

Further characterization of the salicylate forms was performed by LC-MS as well with a Waters Integrity System equipped with a 996 photodiode array detector and Thermabeam Mass Detector. A Waters semi-microbore Nova Pak C8 column (2 mm×10 mm) was equilibrated with 0.5% acetic acid:acetonitrile (95:5, v/v) with a flow of 0.25 mL/min. After injection, a gradient to a final solvent composition of 5:95, v/v, was established over 25 min. The solvent composition was then returned to initial over 2 min and equilibrated for 15 min prior to subsequent injections. With these LC-MS conditions, the retention time of the major metabolite was 12 min and the minor metabolite (not always detectable) was 3 min. The Thermabeam Mass Detector operates with standard electron impact ionization energy of 70 eV and scans from 50 to 700 m/z. The fragmentation pattern of the conjugated forms, as seen in the lower mass ranges (50–100 m/z), suggested the presence of a sugar within the larger molecule. This conclusion was reached by matching these spectra with the Wiley Registry of Mass Spectral Data, $6^{th}$ Ed, John Wiley & Sons, Inc. (1994). Many sugars, however, are characterized by similar fragmentation patterns.

Preliminary analysis of the dried wintergreen extract using β-glucosidase, which is specific for glucose conjugates, showed a 6-fold increase in the release of free salicylate as compared to a 330-fold increase in the release of free salicylate following complete chemical hydrolysis [Enyedi et al., *Proc. Natl. Acad. Sci*., 89:2480–2484 (1992)]. A similar trend was observed for the release of methyl salicylate from this extract. Together, these results indicate that the predominant form of salicylate in wintergreen leaves is not a simple glucose conjugate, but does contain sugar.

Early reports describe gaultherin as a conjugate of methyl salicylate to a disaccharide of xylose and glucose. In order to confirm these observations, an HPLC purified fraction of the major peak was hydrolyzed in 0.5% HCl at 80° C. for 3 hour followed by acetylation at 60° C. for 12 hour with 1 mL of chloroform, 200 mL of acetic anhydride (Supelco, Bellafont Pa.) and 400 mL of glacial acetic acid. Similar acetylations were performed on equimolar mixes of sugars. Only the combination of xylose and glucose showed the same GC-MS profile as the hydrolysis products from the conjugate, thus confirming the identity reported in the literature. In addition, positive fast atomic bombardment (FAB+) analysis of the purified conjugate revealed a molecular ion of 469 m/z. This mass corresponds to the mass of gaultherin (446 m/z) plus a molecule of sodium, which is frequently present in samples.

Results:

The concentrations of free and total SA in various species were measured using stable isotope dilution analysis as described above. Results are shown in Table I.

TABLE I

The amounts of free and total SA in species reported to contain elevated concentrations of SA as measured by stable isotope dilution analysis with GC-MS

| Plant Species | Free SA μg/g FW | Total SA μg/g FW |
| --- | --- | --- |
| English thyme | 0.81 | 31.63 |
| Lemon thyme | 1.55 | 42.32 |
| French thyme | 0.33 | 13.26 |
| Lavender | 0.28 | 6.14 |
| Rosemary | 0.58 | 3.84 |
| Rice M-201 | 1.40 | 9.50 |
| Wintergreen | 19.00 | 5770.00 |

These plants represent just a few of the species examined that have been suggested to contain potentially elevated concentrations of SA as suggested by various literature sources [Perry et al., *Nutrition Reviews*, 54:225–240 (1996), Raskin et al., *Annals of Botany*, 66:369–370 (1990)] and as such could represent alternative sources of natural aspirin. The method of stable isotope dilution analysis provided both precise quantification of SA and chemical identification, independent of sample recovery. A similar method using an unpurified $^2H_3$-SA standard has been described but was limited to the measurement of only free SA [Scott et al., *Phytochemistry*, 37:335–336 (1994)]. The many advantages of stable isotope dilution analysis are critical when examining a diverse variety of plant species. The SA concentrations of the species were generally much lower than reported in the literature, which utilized less precise analytical methods.

No documented varieties or cultivars of wintergreen, *Gaultheria procumbens*, have been described in the literature to our knowledge. However, there were clearly differences in appearance in those plants which were grown on the west coast from those plants which were grown on the east coast. In general, the west coast plants were anatomically larger in height, leaf size, flower size, and berry size. The SA contents of these varieties was examined to determine if there was any correlation between size and salicylate concentration.

TABLE II

Salicylate content of wintergreen varieties

| Salicylate pool | West Coast μg/g FW | East Coast μg/g FW |
| --- | --- | --- |
| Methyl salicylate | 85 | 106 |
| Free salicylic acid | 1,661 | 19 |
| Total salicylate | 10,700 | 5,770 |

Table II shows that the larger variety contains almost twice as much total salicylate per gram fresh weight of tissue. In both varieties, however, the methyl salicylate concentrations were similar and several-fold lower than the total salicylate concentration. Therefore, the bulk of the methyl salicylate must be present in a conjugated form, i.e., gaultherin. The difference in the size of the plants grown on the west coast from those plants grown on the east coast could be attributed to different growing conditions or to slight varietal differences. This distinction cannot yet be made. However, the growing conditions of *Gaultheria procumbens* can have a dramatic effect on the plants' concentrations of salicylate. In general, stresses tend to promote elevated salicylate concentrations in *Gaultheria procumbens*.

Figure 1:
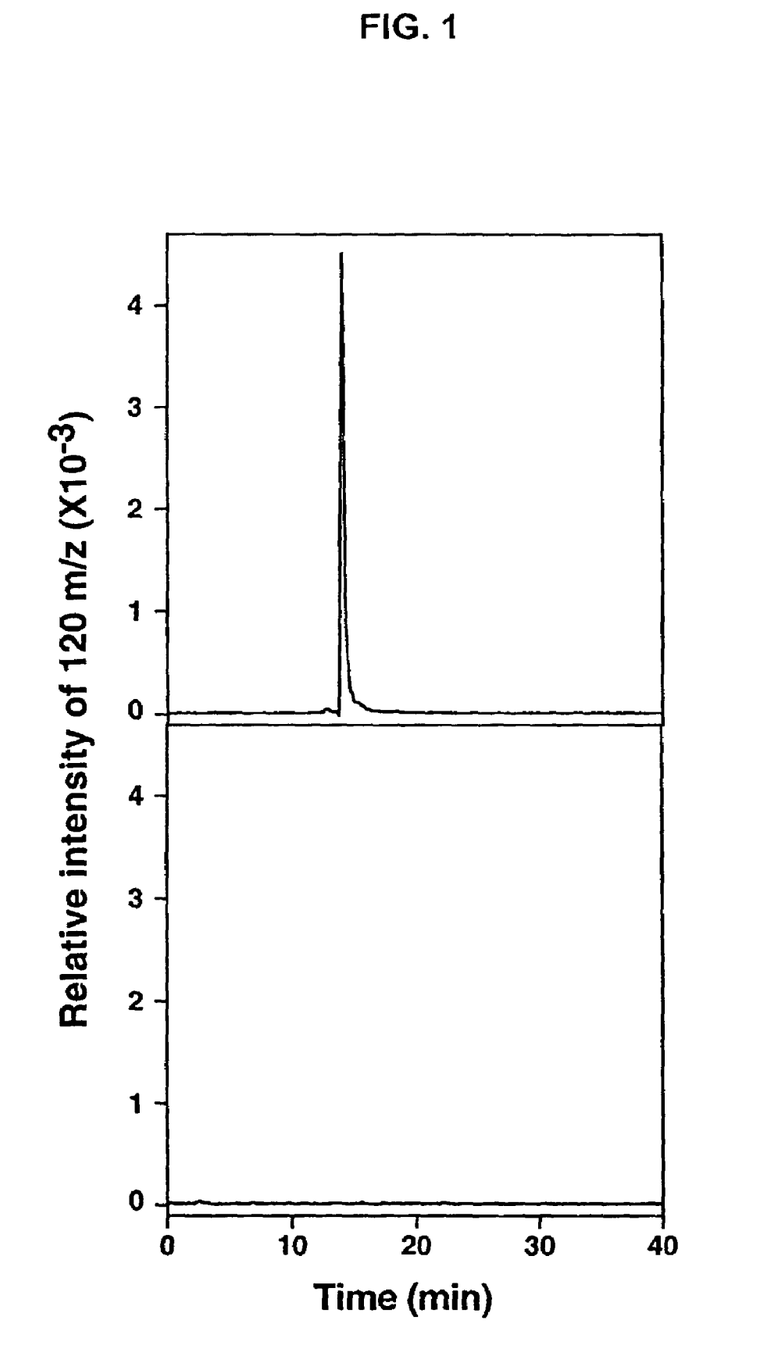
FIG. 1. LC-MS profiles showing comparative stability of gaultherin-containing extracts in methanol (upper panel) and in water (lower panel).
Figure 2:
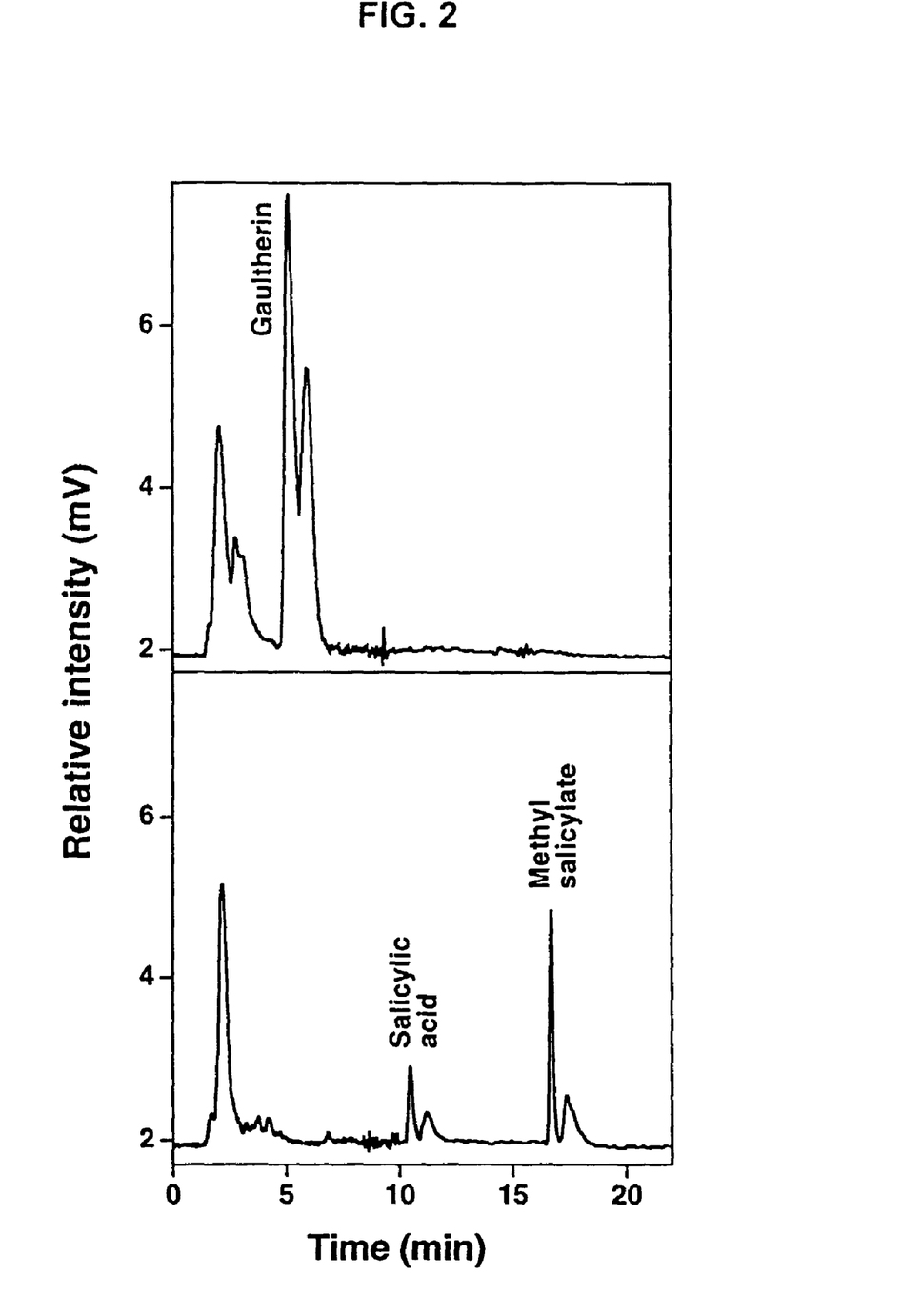
FIG. 2. HPLC profiles showing comparative stability of gaultherin-containing extracts in methanol (upper panel) and in water (lower panel).

Two different kinds of extractions were performed on wintergreen leaf tissue in order to determine the form of the SA in the leaf tissue since the methyl salicylate and free SA concentrations were relatively low compared to the total SA concentration (FIG. 1 and FIG. 2). The HPLC fluorescence profile of water extracted leaves contained only two predominant peaks (in addition to the solvent front) which had retention times and PDA spectra corresponding to SA and free methyl salicylate (FIG. 1). The water extracted sample contains potential products of enzymatic activity after tissue disruption. Methanolic extracts of wintergreen leaves had only one predominant peak (in addition to the solvent front, FIG. 1) which had a very early retention time compared to SA and methyl salicylate. Only very small peaks representing SA and methyl salicylate were observed in the methanolic extracts. It may be that the methanol denatures proteins (e.g., the enzyme gaultherase) and thus prevents degradation of metabolites from enzymatic activity. The dominant presence of one peak with fluorescence suggested that it would consist of a bound form of SA. These extraction results predict a high concentration of bound SA present in the wintergreen tissue. The bound SA seems to be protected from enzymatic activity when extracted in methanol; however, this form may be degraded upon extraction in water because of the presence of active enzymes in the plant tissues.

Figure 3A:
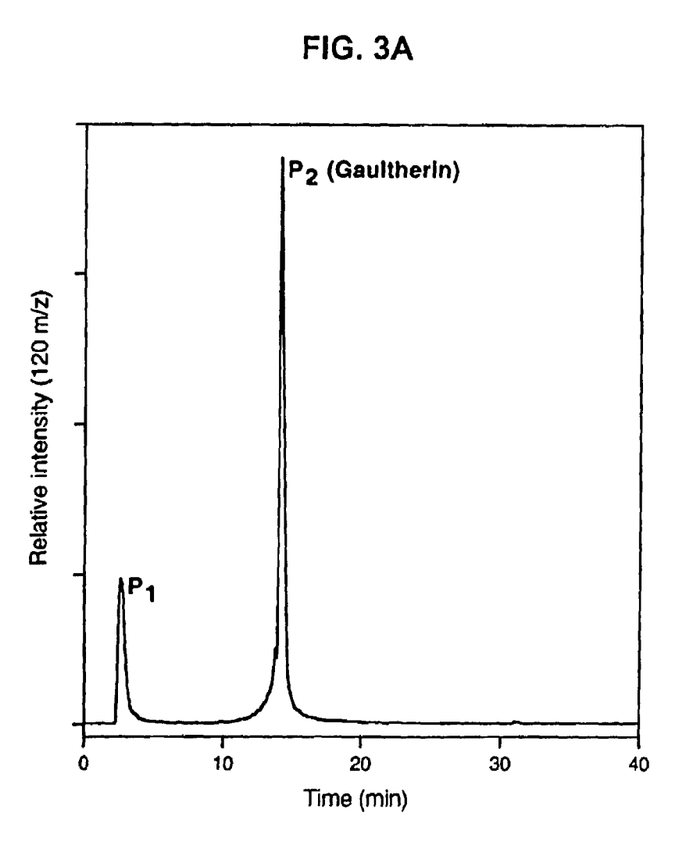
FIG. 3A: LC-MS profile of gaultherin, showing a major peak (P2) identified as gaultherin and a minor peak (P1) presumed to be a gaultherin variant.
Figure 3B:
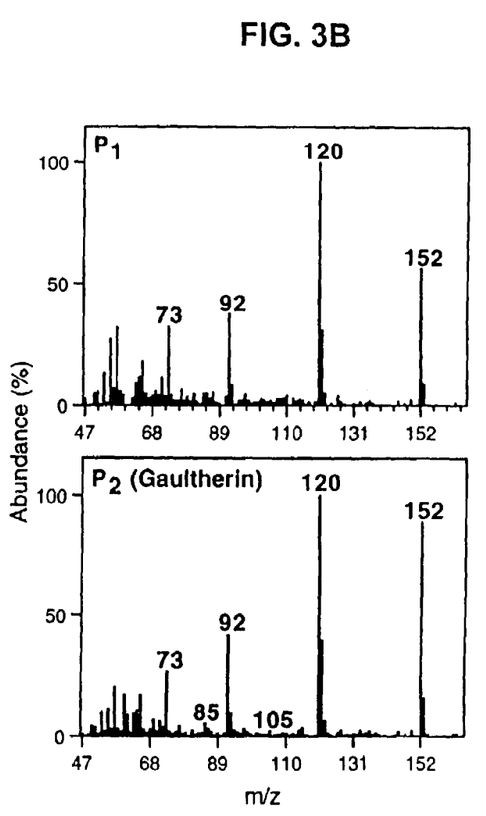
FIG. 3B: Mass spectrograms of P1 and P2.

The unknown which was presumed to be a bound form of SA was further characterized by LC-MS. The use of a shallow gradient and semi-microbore column was able to extend the retention time of this metabolite and provide enhanced chromatography as shown in FIG. 3. This bound form of SA was also resolved into 2 forms, abbreviated P1 and P2. P1 was a minor form which was not always present in alcoholic extracts, but could represent an important additional metabolite. Both P1 and P2 were characterized by similar mass spectra. The most noteworthy feature of these spectra is that they consist primarily of the fragmentation pattern of methyl salicylate. The molecule of methyl salicylate would never be visible by LC-MS as methyl salicylate is a volatile molecule which would be lost during desolvation, prior to MS ionization. The loss of volatile analytes during desolvation has been extensively observed. The occurrence of a molecule which contains the ion fragments associated with methyl salicylate by LC-MS would result only from the fragmentation of a molecule which contains methyl salicylate as part of a larger chemical structure with lower volatility. Many of the smaller ions of these spectra (less than 92) are not characteristic of the fragmentation pattern of methyl salicylate and are likely to represent ions from the non-methyl salicylate portion of the larger molecule. In general, these smaller ions are typical fragments from sugars, as suggested by comparison between those of the Wiley Registry of Mass Spectral Data, 6$^{th}$ Ed., John Wiley & Sons, Inc. (1994). Many simple sugars possess similar spectra which prevents the determination of their precise structure from this data alone. The fragmentation pattern of these forms by LC-MS is, therefore, consistent with a sugar conjugate of methyl salicylate. No molecular ion seems to be present in these spectra which would also be indicative of sugar conjugates that are commonly unable to survive electron impact ionization without fragmentation.

Various species were investigated for comparative purposes and as potential new sources of natural aspirin as shown in Table III.

TABLE III

Gaultherin and salicylate content of select species

| Plant Species | Gaultherin µg/g FW | Total Salicylate µg/g FW |
|---|---|---|
| Gaultheria procumbens | 26,000* | 10,700 |
| Gaultheria shallon | n.d. | 1.2 |
| Filipendula ulmaria | n.d. | 479 |

*based on extract concentrations
n.d. = not detectable

*Gaultheria shallon* is a close relative of *Gaultheria procumbens* but has the advantage of much greater biomass. *Gaultheria shallon* does not contain measurable concentrations of gaultherin and has very small concentrations of total salicylate as well. *Filipendula ulmaria* is not a related species, but has been reported in the literature to be the original source of natural aspirin used by ancient peoples [Balick et al., eds., *Plants, People and Culture, Scientific American Library*, New York, p. 32, 1997]. This contrasts other literature which portrays willow as the original source of aspirin [Pierpoint, *In Advances in Botanical Research*, 20:164–235 (1994)]. *Filipendula uliaria* does contain elevated concentrations of total salicylate, as compared to the species in Table I, albeit much lower than those found in *Gaultheria procumbens*. *Filipendula* does not, however, contain measurable concentrations of gaultherin. Only the leaves of this species were examined, not the roots or the berries which may have additional forms. The concentrations within the leaves were very low when compared to *Gaultheria procumbens* and did not warrant further investigation. Moreover, as shown in Table III, *Gaultheria procumbens* contains twenty times more total salicylate per gram of fresh weight tissue than *Filipendula* plants.

*Gaultheria procumbens* is the richest source of total salicylate as determined using our methods of stable isotope dilution with the plant species mentioned above. All of the previous investigations were performed with leaf tissue only, which may not be the only tissues which contain high concentrations of salicylate. Use of the entire plant above the ground, however, would be ideal for practical reasons of harvest. Therefore, each of the tissues was examined for total salicylates content as shown in Table IV.

TABLE IV

Total salicylate content of wintergreen tissues

| Tissue | SA (µg/g FW) |
|---|---|
| Leaves | 3,832 |
| Flowers | 6,425 |
| Stems | 2,227 |
| Berries | 1,491 |

All of the tissues examined contained substantial concentrations of salicylate as compared to other species (Table I & Table IV), the flowers being the organ which seems to contain the highest concentration. The specific form of salicylates within each tissue was not determined. The results from the analysis of the leaves suggest that the gaultherin conjugate would be the most prevalent form.

Further measurements were performed with alcoholic extracts of *Gaultheria procumbens*. A variety of alcohols were used for the efficient extraction of gaultherin which include methanol, ethanol, and isopropanol. The concentration of total salicylate within these dried extracts ranged from 37 to 60 mg/g (average of 5 wt. %) as measured using stable isotope dilution analysis by GC-MS. As measured by HPLC and LC-MS, the concentration of total salicylate was determined to correspond to a gaultherin concentration range of 120–180 mg/g (average of 15 wt. %). Based on the difference in mass of salicylic acid and gaultherin, which is 3.2 times, these two ranges agree closely. Therefore, not only do these samples contain high concentrations of total salicylate and gaultherin, but the close agreement of these concentrations predicts that most of the salicylate present must be in the form of gaultherin.

In this example, the identity of gaultherin was verified using modern analytical methods including GC-MS and LC-MS. Methods were also defined for the precise quantification of SA, methyl salicylate, and total salicylate using stable isotope dilution technologies. A systematic measurement of the individual salicylates in wintergreen has not previously been performed. These methods have been used to measure salicylate concentrations in various species and determine that *Gaultheria procumbens* is the richest plant source of gaultherin.

The predominant form of salicylate in *Gaultheria procumbens* is gaultherin, which is easily hydrolyzed upon tissue disruption. This hydrolysis can be prevented, however, with proper extraction in alcohol or other solvent, which presumably inactivates the activity of gaultherase and leads to the production of extracts containing as much as 18 wt. % gaultherin.

EXAMPLE 2

Gaultherin-Containing Extracts Reduce Platelet Aggregation

Wintergreen extract containing gaultherin is a rich natural source of salicylate. In this example, wintergreen is extracted to provide a gaultherin-containing composition. The wintergreen-derived extract should provide pharmacological activities similar to aspirin, which is routinely taken for cardiovascular and/or cardiopulmonary benefit because of is ability to reduce platelet aggregation, and therefore the risk of blood clotting that could lead to a heart attack or stroke.

The wintergreen-derived extract, an exemplification of a gaultherin-containing extract, was evaluated for its ability to prevent platelet aggregation in vitro. Platelet aggregation was quantified by measuring the turbidity of the solution with an optical aggregometer, which measures changes in turbidity such as those associated with increasing platelet aggregation. A maximum non-reversible decrease in the aggregation response of greater than 50% is considered significant. The wintergreen-derived gaultherin-containing extract had 100% antagonist activity at 5 mM, i.e., no aggregation was observed after treatment with gaultherin.

Methods:

In vitro assay: Venous blood from New Zealand rabbits (2.5–3 kg) was mixed with one-tenth volume of 0.13 M trisodium citrate and centrifuged at 220 g. Gaultherin-containing extract was then added to the platelet-rich plasma alone or with platelet-activating factor and compared in order to measure any possible platelet-activating factor agonist activity. Any increase in aggregation in the presence of the extract relative to its absence would be attributed to an antagonist activity caused by the addition of the gaultherin-containing composition. [Nunez et al., *European Journal of Pharmacology*, 123:197–205 (1986)] Any decrease in aggregation time in the presence of the extract relative to its absence would be-indicative of a platelet-activating agonist activity attributable to the extract. No agonist activity was observed. Gaultherin-containing extract with platelet-activating factor was then added to the plasma and compared to the aggregation activity of the platelet-activating factor alone to measure antagonist activity. The gaultherin-containing extract had 100% antagonist activity at 5 mM.

Wintergreen-derived gaultherin containing extracts were also shown to inhibit platelet aggregation in vivo. As shown in Table V, gaultherin-containing extracts prevented platelet aggregation in vivo, as measured by the bleeding time in mouse tail tips [Dejana et al., *Thrombosis Research.*, 15:191–197 (1979), Butler et al., *Thrombosis Hemostasis* 47: 46–49 (1982)]. The gaultherin-containing extract prolonged mouse bleeding times assessed at 1, 3, and 6 hours after treatment. Therefore, gaultherin-containing extracts prevent platelet aggregation in vitro and in vivo.

In vivo assay: The gaultherin-containing extract was mixed with vehicle (2% Tween 80/distilled water) and orally administered to 5 ICR rats (22+2 g) at the doses given in Table V. After 1, 3, or 6 hours of treatment, the mice were suspended in holders and 0.5 mm of the tip of each tail was transected and immersed in a test tube containing saline at 37° C. The bleeding time is defined as the time required for the bleeding to cease for a period of greater than 15 seconds. Prolongation of the bleeding time over that of control animals was then calculated. Aspirin was used as the standard to ensure that the assay was performing as expected.

TABLE V

Effect of Wintergreen Extract on Bleeding Time in Mice

| Treatment | Dose | Pre-treatment Time (h) | Avg. Bleed Time (sec) | | Prolongation (%) | |
|---|---|---|---|---|---|---|
| | | | Exp. 1 | Exp. 2 | Exp. 1 | Exp. 2 |
| Vehicle | 20 ml/kg | 1 | 60 | 66 | — | — |
| Aspirin | 100 mg/kg | 1 | 120 | 114 | 100 | 73 |
| W. Extract | 5000 mg/kg | 1 | 82 | | 37 | |
| W. Extract | 5000 mg/kg | 3 | | 67 | | 2 |
| W. Extract | 5000 mg/kg | 6 | | 85 | | 29 |

EXAMPLE 3

Lesser Amount of Gastric Irritation Caused by Gaultherin-Containing Extract Than Aspirin A common side effect of chronic salicylate use is stomach irritation, for which aspirin is well noted. Because gaultherin is a highly derivatized form of salicylate, its use should result in less gastric irritation than the use of aspirin. The effect of a gaultherin-containing compositions, e.g., wintergreen extract, on the stomach lining was therefore compared to that of aspirin (Table VI).

Wintergreen-derived, gaultherin-containing extract and aspirin were given by oral gavage to overnight-fasted Wistar rats (200+/−20 g). The 5000 mg/kg dose of wintergreen extract and the 150 mg/kg dose of aspirin used in the experiment contain equal total amounts of salicylate. Four hours after treatment, the stomach lining was harvested and scored for gastric irritation [Guth et al., *Gastroenterology*, 76: 88–93 (1979)]. A score of zero was given for no sign of hyperaemia (excess blood or engorgement with blood) or bleeding. A score of one was given when hyperaemia was evident. A score of two was given when some spot bleeding was observed. A score of three was assigned for any hyperaemia and spot bleeding and a score of four for hyperaemia and spot bleeding occurred over the entire stomach. The total aspirin score for three rats was nine as all three rats experienced some hyperaemia and spot bleeding. The total wintergreen-derived, gaultherin-containing extract score was two because only two of the three rats were noted to have some hyperaemia. Based on these responses, the gastric irritation caused by wintergreen extract was substantially less (approximately five times lower) than that caused by aspirin.

TABLE VI

Gastric Irritation in Fasted Rats

| Treatment | Dose | Total Score | Response (%) |
|---|---|---|---|
| Vehicle | 10 ml/kg | 0 | 0 |
| Wintergreen-derived, gaultherin-containing extract | 5000 mg/kg | 2 | 22 |
| Aspirin | 150 mg/kg | 9 | 100 |

EXAMPLE 4

Gaultherin-Containing Extracts Reduce Inflammatory Responses

A hind paw inflammatory rat model was used to test the analgesic potential of a gaultherin-containing composition derived from wintergreen relative to Naproxen (standard control) as shown in Table 4. Wintergreen-derived gaultherin-containing extract was administered by per-oral gavage at human dose equivalents of 200 mg and 400 mg per day and Naproxen was administered at a dose of 440 mg per day. Male Sprague-Dawley rats (300–350 grams) were treated for 5 days by gavage. Inflammation (edema and hyperalgesia) was induced 3 days prior to treatment through intraplantar injection of Freund's adjuvant (containing 170 μg *Mycobacterium butyricum*). Edema was determined by physical measurements of paw thickness and ankle width. Pain tolerance (i.e., pain reduction) was mechanically assessed via digital Von Frey determinations using a series of measurements at 6 locations on the surface of a paw. [Ren et al., *ILAR Journal*, 40(3):1–12 (1999), Kayser et al., *Pain*, 28:99–107 (1987)] Measurement terminated at the point of paw withdrawal, auditable indication of discomfort, or animal shuddering. Measurements were performed on left and right paws. Naproxen showed a predictable anti-inflammatory and analgesic effect. Gaultherin also showed improvements in pain tolerance (i.e., 6.7% and 9.9% at human dose equivalents of 200 mg and 400 mg, respectively). At the same dose concentrations, gaultherin reduced edema by 12.2% and 16.9%, respectively, in contrast to a 28% reduction for Naproxen. Gaultherin-containing extracts can, therefore, be used as an anti-inflammatory therapeutic. Further, gaultherin-contaiining extracts can be used in preventive methods, particularly useful for subjects, human and non-human, at risk of developing an inflammatory response.

TABLE VII

Effect of Gaultherin-containing Extract in the Rat Hind Paw Edema Model

| Treatment | Dose | Edema reduction (%) |
|---|---|---|
| Wintergreen-derived Extract (2.5% gaultherin) | 200 mg/day for 5 days | 12 |
| Wintergreen-derived Extract (2.5% gaultherin) | 400 mg/day for 5 days | 17 |
| Naproxen (100% active) | 440 mg/day for 5 days | 28 |

EXAMPLE 5

Use of Gaultherin-Containing Extract to Treat Cancer

Protocol for the Treatment of Cancer

A gaultherin-containing composition may also be used in the treatment of any cancer in which the inhibition of cyclooxygenase may have an ameliorative effect. Initially, one may verify this effect by contacting a model cancer cell line with the gaultherin-containing compositions of the present disclosure. If the compositions inhibit the cell growth, and/or expression of tumor-specific markers in that model cancer cell, the compositions may prove effective in in vivo cancer treatment regimens. Initially, such in vivo regimens will preferably be verified in animal models of cancer, e.g., various cancer cells transplanted into a nude mouse model. Once such studies have been used to verify the anti-cancer regimens, the compositions are used in the treatment of an individual exhibiting a cancer. An "individual" as used herein, is a vertebrate, preferably a mammal, more preferably a human. Mammals include research, farm and sport animals, pets, and the like.

In the anti-cancer treatment embodiments of the present disclosure, the composition is typically administered orally or parenterally in dosage unit formulations containing standard, well known non-toxic physiologically acceptable carriers, adjuvants, and vehicles as desired. The term parenteral as used herein includes subcutaneous injections, intravenous, intramuscular, intra-arterial injection, and infusion techniques. The gaultherin composition may be delivered to the patient alone or in combination with other therapies used to combat the cancer. Where a combination therapy is contemplated, the gaultherin composition may be administered before, after, or concurrently with, the other anti-cancer agents.

A typical treatment course may comprise about six doses delivered over a 7- to 21-day period. Upon election by the clinician, the regimen may be continued at six doses every three weeks, or on a less frequent (monthly, bimonthly, quarterly, and the like) basis. Of course, these are only exemplary treatment schedules, and the skilled practitioner will readily recognize that many other schedules are possible. The suitability in each case of such schedules, and the aforementioned modes of administration are determined by those of skill in the art, using no more than routine procedures.

In one embodiment, administration simply entails injection of the therapeutic composition into the tumor. In another embodiment, a catheter is inserted into the site of the tumor and the cavity may be continuously perfused for a set period of time or until results are achieved.

Clinical responses are preferably defined using standard criteria in the art. For example, a complete response may be defined by the disappearance of all measurable disease for at least one month. Similarly, a partial response may be defined by a 50% or greater reduction in the sum of the products of perpendicular diameters of all evaluable tumor nodules for at least one month, with no tumor sites showing enlargement. A mixed response may be defined by a reduction in the sum of the products of perpendicular diameters of all measurable lesions by 50% or greater, with enlargement of one or more sites.

As one of skill in the art would recognize, accumulated experience with the above-described treatment regimes is used to adjust the regimes to optimize results in a given situation. Those of skill in the art will be able to take the information disclosed in this specification and optimize treatment regimes based on clinical trials performed in accordance with the specification.

Clinical Trials of the Use of Gaultherin Containing Compositions in Treating Cancers This example discloses human cancer treatment protocols using the gaultherin-containing compositions of the present disclosure. Such drug treatment will be of use in the clinical treatment of various cancers in which cyclooxygenase inhibition results in an amelerioration, inhibition, or other loss of a transformed or cancerous phenotype. Such treatment methods are particularly useful tools in anti-tumor therapy, for example, in treating patients with ovarian cancer, breast cancer, an adenocarcinoma, or any other cancer in which a cyclooxygenase plays a role. Such cancers may or may not be resistant to conventional chemotherapeutic regimens.

The various elements of conducting a clinical trial, including patient treatment and monitoring, will be known to those of skill in the art in light of the present disclosure. The following information is presented as a general guideline for use in establishing the efficacy of gaultherin efficacy in clinical trials.

Patients with advanced, metastatic cancer are chosen for clinical study. Measurable disease is not required; however, the patient should preferably have easily accessible pleural effusion and/or ascites.

In an exemplary clinical protocol, patients undergo placement of a Tenckhoff catheter, or other suitable device, in the pleural or peritoneal cavity and undergo serial sampling of pleural/peritoneal effusion. Preferably, patients or subjects will exhibit an absence of known loculation of the pleural or peritoneal cavity, creatinine levels that are below 2 mg/deciliter (dl), and bilirubin levels that are below 2 mg/deciliter (dl). The patient/subject preferably exhibits a normal coagulation profile.

In regard to the gaultherin composition and/or other anti-cancer drug administration, a Tenckhoff catheter or alternative device may be placed in the pleural cavity or in the peritoneal cavity. A sample of pleural or peritoneal fluid can be obtained, so that baseline cellula activity, cytology, lactate dehydrogenase (LDH), and appropriate markers in the fluid (CEA, CA15-3, CA 125, p185) and in the cells (p185) may be assessed and recorded.

A gaultherin-containing commposition may be administered alone or in combination with another chemotherapeutic agent. The administration may be in the pleural/peritoneal cavity, directly into the tumor, or administered systemically, using routes known in the art. An initial dose is about 0.5 mg/kg body weight. Three patients are treated at each dose level in the absence of toxicity exceeding grade III. Toxicity is generally categorized as grade 0 (no toxicity), grade I (mild toxicity), grade II (moderate toxicity), grade III (severe toxicity), and grade IV (intolerable toxicity) [Miller et al., Cancer, 47(1):207–214 (1981)]. Dose escalation is achieved by 100% increments (0.5 mg, 1 mg, 2 mg, 4 mg) until drug-related grade II toxicity is detected. Thereafter, dose escalation proceeds by, e.g., 25% increments. The administered dose may be fractionated equally into two infusions, separated by six hours if the endotoxin levels for the single dose is determined to exceed 5EU (endotoxin units)/kg for any given patient.

The gaultherin composition optionally in combination with an anti-cancer agent, may be administered over a short infusion time or at a steady-rate of infusion over a 7- to 21-day period. The gaultherin composition infusion may be administered alone or in combination with the anti-cancer drug. The infusion dose is determined with the twin considerations of efficacy and toxicity in mind, using routine optimization procedures. If grade II toxicity were reached after any single infusion, or at a particular period of time for a steady-rate infusion, further doses would be adjusted to avoid undesirable toxicity levels. Increasing doses of gaultherin composition in combination with an anti-cancer drug are administered to groups of patients until approximately 60% of patients show unacceptable grade III or IV toxicity in any category. Doses known in the art that are a fraction of this value (e.g., 67%) are defined as a safe dose.

Physical examination, tumor measurements, and laboratory tests are desirably initiated before treatment and continued for about 3–4 weeks after treatment. Laboratory studies optimally include complete blood count (CBC), differential and absolute platelet count, urinalysis, Sequential Multiple Analyzer tests ("SMA-12-100") (liver and renal function tests), coagulation profile, and any other appropriate chemistry studies to determine the extent of disease, or to determine the cause of symptoms presented. Also, appropriate biological markers in serum should be monitored, e.g. carcinoembryonic antigen (CEA), carbohydrate antigen (CA 15-3), for breast cancer, the protein with a molecular weight of 185,000 daltons p185) encoded by HER-2/neu oncogene, also referred to as c-erbB-2, and for ovarian cancer antigen 125 (CA 125), and p185.

To monitor the course of a disease and to evaluate anti-tumor responses, it is contemplated that patients or subjects of a disease are examined for appropriate tumor markers about every 4 weeks, with twice-weekly CBC, differential and platelet counts for the 4 weeks. If no myelosuppression has been observed during the approximately four-week monitoring period, the frequency may be reduced to a weekly schedule for periods determined by the clinician in view of all relevant factors in a given situation. If any patient has prolonged myelosuppression, a bone marrow examination is advised to rule out the possibility of tumor cell invasion of the marrow as the cause of the myelosuppression. A coagulation profile is optimally obtained about every 4 weeks. An SMA-12-100 is optimally performed weekly. Pleural/peritoneal effusion may be sampled 72 hours after the first dose, weekly thereafter for the first two courses, and every 4 weeks thereafter until progression or off study. Cellularity, cytology, LDH, and appropriate markers in the fluid (CEA, CA15-3, CA 125, p185) and in the cells (p185) are optimally assessed. When measurable disease is present, tumor measurements are recorded about every 4 weeks. Appropriate radiological studies should be repeated every 8 weeks to evaluate tumor response. Spirometry and lung diffusing capacity tests (DLCO) may be repeated 4 and 8 weeks after initiation of therapy and at the time study participation ends. A urinalysis is optimally performed about every 4 weeks.

Clinical responses are defined by any acceptable measure known in the art. For example, a complete response may be defined by the disappearance of all measurable disease for at least one month. Analogously, a partial response may be defined by a 50% or greater reduction in the sum of the products of perpendicular diameters of all evaluable tumor nodules for at least one month with no tumor sites showing enlargement. Similarly, a mixed response may be defined by a reduction in the sum of the products of perpendicular diameters of all measurable lesions by 50% or more, with enlargement at one or more sites.

The present disclosure is not limited to the embodiments described and exemplified above, but is capable of variation and modification without departure from the scope of the appended claims.

What is claimed is:

1. A method of increasing serum salicylic acid concentration comprising:
    administering a therapeutically effective amount of a gaultherin-containing composition to an individual wherein the gaultherin-containing composition is isolated from a plant tissue.

2. The method of claim 1, wherein the plant tissue is obtained from *Gaultheria procumbens*.

3. The method of claim 1, wherein the gaultherin content of the gaultherin-containing composition is obtained in an amount of at least 5 mg gaultherin per gram fresh weight of plant tissue.

4. The method of claim 1, wherein the gaultherin content of the gaultherin-containing composition is obtained in an amount of at least 15 mg gaultherin per gram fresh weight of plant tissue.

5. The method of claim 1, wherein the individual is a mammal.

6. The method of claim 1, wherein the individual is a human.

7. The method of claim 1, wherein the gaultherin-containing composition is administered orally and causes less gastric irritation than an equivalent dose of actyl salicylic acid as measured by the respective salicylate contents.

8. The method of claim 1, wherein the individual has a condition selected from the group consisting of an inflammatory condition, a cardiovascular condition, and a cancerous condition.

* * * * *

UNITED STATES PATENT AND TRADEMARK OFFICE
CERTIFICATE OF CORRECTION

PATENT NO. : 7,033,618 B2
APPLICATION NO. : 10/338312
DATED : April 25, 2006
INVENTOR(S) : Ribnicky et al.

Page 1 of 1

It is certified that error appears in the above-identified patent and that said Letters Patent is hereby corrected as shown below:

On the Title Page:

At Field (75), 1st Inventor, "David Ribnicky, Plainsboro, NJ" should be -- David Ribnicky, North Branch, NJ --.

In the Claims:

At Column 22, line 18 claim 7, "actyl salicylic" should be -- acetyl salicylic --.

Signed and Sealed this

Twenty-ninth Day of April, 2008

JON W. DUDAS
*Director of the United States Patent and Trademark Office*